US011810303B2

United States Patent
Meyers et al.

(10) Patent No.: US 11,810,303 B2
(45) Date of Patent: Nov. 7, 2023

(54) SYSTEM ARCHITECTURE AND METHOD OF PROCESSING IMAGES

(71) Applicant: Purdue Research Foundation, West Lafayette, IN (US)

(72) Inventors: Brett Albert Meyers, West Lafayette, IN (US); Pavlos P. Vlachos, West Lafayette, IN (US); Melissa Brindise, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 215 days.

(21) Appl. No.: 17/199,006

(22) Filed: Mar. 11, 2021

(65) Prior Publication Data
US 2021/0287375 A1  Sep. 16, 2021

Related U.S. Application Data

(60) Provisional application No. 62/987,978, filed on Mar. 11, 2020.

(51) Int. Cl.
| | |
|---|---|
| *G06T 7/11* | (2017.01) |
| *G06T 7/174* | (2017.01) |
| *G06T 7/136* | (2017.01) |
| *G06T 7/90* | (2017.01) |
| *G06T 7/40* | (2017.01) |
| *G16H 30/40* | (2018.01) |
| *G06T 7/187* | (2017.01) |

(52) U.S. Cl.
CPC ............... *G06T 7/11* (2017.01); *G06T 7/136* (2017.01); *G06T 7/174* (2017.01); *G06T 7/187* (2017.01); *G06T 7/40* (2013.01); *G06T 7/90* (2017.01); *G16H 30/40* (2018.01); *G06T 2207/20101* (2013.01); *G06T 2207/30048* (2013.01)

(58) Field of Classification Search
CPC . G06T 7/11; G06T 7/136; G06T 7/174; G06T 7/187; G06T 7/40; G06T 7/90; G06T 2207/20101; G06T 2207/30048; G06T 2207/10132; G06T 7/0016; G06T 7/12; G16H 30/40
See application file for complete search history.

(56) References Cited

U.S. PATENT DOCUMENTS

| | | |
|---|---|---|
| 9,629,615 B1 | 4/2017 | Tavakoli et al. |
| 2002/0072670 A1 | 6/2002 | Chenal et al. |
| 2002/0072671 A1 | 6/2002 | Chenal et al. |

(Continued)

OTHER PUBLICATIONS

Sarvaiya et al., "Image Registration Using Log Polar Transform and Phase Correlation to Recover Higher Scale", 2012, Journal of Pattern Recognition Research, 90-105 (Year: 2012).*

(Continued)

*Primary Examiner* — Chan S Park
*Assistant Examiner* — Daniel C Chang
(74) *Attorney, Agent, or Firm* — Purdue Research Foundation

(57) ABSTRACT

The present application relates to an automated segmentation method for use with echocardiograms (echo). The method uses an iterative Dijkstra's algorithm, a strategic node selection, and a novel cost matrix formulation based on intensity peak prominence and is this termed the "Prominence Iterative Dijkstra's" algorithm, or ProID.

18 Claims, 13 Drawing Sheets

(56) References Cited

U.S. PATENT DOCUMENTS

| | | | |
|---|---|---|---|
| 2008/0095417 A1 | 4/2008 | Pedrizzetti et al. | |
| 2015/0133802 A1 | 5/2015 | Nabutovsky et al. | |
| 2015/0206323 A1 | 7/2015 | Lee et al. | |
| 2016/0098833 A1 | 4/2016 | Tsadok et al. | |
| 2017/0065242 A1* | 3/2017 | Chirvasa | A61B 6/466 |
| 2019/0125309 A1 | 5/2019 | Ramm et al. | |
| 2019/0205478 A1* | 7/2019 | Cavallo | G06F 18/00 |
| 2019/0328364 A1 | 10/2019 | Questa et al. | |
| 2020/0193603 A1* | 6/2020 | Golden | G06T 7/149 |
| 2021/0100526 A1 | 4/2021 | Schein et al. | |

OTHER PUBLICATIONS

Eckstein, A. et al., "Assessment of Advanced Windowing Techniques for Digital Particle Image Velocimetry (DPIV)," Meas. Sci Technol., vol. 20, No. 7, p. 075402, 2009.

Meyers, B. A. et al., "Development and Validation of a Phase-Filtered Moving Ensemble Correlation for Echocardiographic Particle Image Velocimetry," Ulrasound in Medicine & Biology, vol. 44, No. 2, pp. 477-488, 2018.

Eckstein, A. et al., "Digital Particle Image Velocimetry (DPIV) Robust Phase Correlation" Meas. Sci. Technol., vol. 20, No. 5, p. 055401, 2009.

Eckstein, A. C. et al., "Phase Correlation Processing for DPIV Measurements," Exp. Fluids, vol. 45, No. 3, pp. 485-500, 2008.

Alessandrini, M. et al., "Generation of Ultra-realistic Synthetic Echocardiographic Sequences to Facilitate Standardization of Deformation Imaging," in 2015 IEEE 12th International Symposiumon Biomedical Imaging (ISBI), 2015, vol. 2015—Jul., No. Sep., pp. 756-759.

Thomas, J. D. et al., "EACVI-ASE-Industry Initiative to Standardize Deformation Imaging: A Brief Update from the Co-chairs," European Heart Journal—Cardiovascular Imaging, vol. 14, No. 11, pp. 1039-1040, 2013.

D'Hooge, J. et al., "Two-dimensional Speckle Tracking Echocardiography: Standardization Efforts Based on Synthetic Ultrasound Data," European Heart Journal—Cardiovascular Imaging, vol. 17, No. 6, pp. 693-701, 2015.

Mirea, O. et al., "Intervendor Differences in the Accuracy of Detecting Regional Functional Abnormalities: A Report from the EACVI-ASE Strain Standardization Task Force," JACC: Cardiovascular Imaging, vol. 11, No. 1, pp. 25-34, 2018.

Mirea, O. et al., "Variability and Reproducibility of Segmental Longitudinal Strain Measurement: A Report from the EACVI-ASE Strain Standardization Task Force," JACC: Cardiovascular Imaging, vol. 11, No. 1, pp. 15-24, 2018.

Alessandrini, M. et al., "A Pipeline for the Generation of Realistic 3D Synthetic Echocardiographic Sequences: Methodology and Open-Access Database," IEEE Transactions on Medical Imaging, vol. 34, No. 7, pp. 1436-1451, 2015.

Bell, M. A. L. et al. "Short-Lag Spatial Coherence Imaging of Cardiac Ultrasound Data: Initial Clinical Results," Ultrasound in Medicine and Biology, vol. 39, No. 10, pp. 1861-1874, 2013.

Farsalinos, K. E., "Head-to-Head Comparison of Global Longitudinal Strain Measurements Among Nine Different Vendors: The EACVI/ASE Inter-Vendor Comparison Study," Journal of the American Society of Echocardiography, 2015; synopsis (full version available in the Journal of the American Society of Echocardiography, vol. 28, No. 10, pp. 1171-1181.e2).

Sarvaiya, J. N. et al., "Image Registration Using Log Polar Transform and Phase Correlation to Recover Higher Scale," Journal of Pattern Recognition Research, vol. 7, No. 1, pp. 90-105, 2012.

Anderson et al., Beginner's Guide to Strain: What should be in your lab in 2018, (2018), asecho.org/wp-content/uploads/2018/01/Anderson-Beginners-Giude-to-Strain.pdf, pp. 1-18.

Becker et al., Analysis of myocardial deformation based on pixel tracking in two dimensional echocardiographic mages enables quantitative assessment of regional left ventricular function, (2006), pp. 1102-1108.

Biering-Sørensen et al., Global Longitudinal Strain by Echocardiography Predicts Long-Term Risk of Cariovascular Morbidity and Mortality in a Low-Risk General Population, The Copenhagen City Heart Sudy, 2017, DOI: 10.1161/CIRCIMAGING.116.005521, pp. 1-11.

Karlsen et al., Global longitudinal strain is a more reproducible measure of left ventricular function than ejection fraction regardless of echocardiographic training, (2019), doi: 10.1186/s12947-019-0168-9, pp. 1-12.

Chan et al., Left ventricular Global-Strain Analysis by Two Dimensoial Speckle Tracking Echocardiography, (2017), asecho.org/wp-content/uploads/2021/10/Left-Ventricular-Global-Strain-Analysis-by-Two-Dimentional-Speckle-Tracking-Echocardiography_-The-Learning-Curve-PIIS0894731717304698.pdf, pp. 1081-1090.

Pedrizzetti et al., Principles of cardiovascular magnetic resonance feature tracking and echocardiographic speckle tracking for informed clinical use, (2016), Pedrizzetti et al., Journal of Cardiovascular Magnetic Resonance, (2016), DOI: 10.1186/s12968-016-0269-7, pp. 1-12.

* cited by examiner

SYSTEM ARCHITECTURE AND METHOD OF PROCESSING IMAGES

CROSS-REFERENCE TO RELATED APPLICATIONS

The present U.S. patent application is related to and claims the priority benefit of U.S. Provisional Patent Application Ser. No. 62/987,978, filed Mar. 11, 2020, the contents of which is hereby incorporated by reference in its entirety into this disclosure.

BACKGROUND

B-mode echocardiography is the leading non-invasive imaging modality to examine left ventricle (LV) health due to its availability, affordability, and ease-of-use. Physicians can assess LV shape and function using a B-mode apical four-chamber long-axis (A4C) cine recording, obtaining end-systolic volume (ESV), end-diastolic volume (EDV), stroke volume, ejection fraction (EF), and cardiac output measurements. Such measurements require an accurate segmentation of the LV boundary. Currently, manual segmentation is the most commonly used clinical approach even though it introduces high inter- and intra-user variability, requires expert training, and is time-consuming to perform.

To mitigate these limitations and ensure repeatable measurements, semi- and fully-automated segmentation tools have been proposed for more than 30 years. Contour detection algorithms fit deformable models or curves to intensity-based features, such as image edges. Favorably, these methods typically have a straightforward implementation and low computational cost. However, they have limited success as the transducer position, noise, and signal loss can corrupt segmented boundaries. Active contour methods have been proposed to overcome these limitations. In general, these tools are reliable, reporting similarities to trained clinicians of 92%-97%.

Deep learning segmentation methods have also been proposed. Unlike shape prior methods, these tools perform unsupervised learning based on image information. Conventional art has used a two-stage, deep neural network which first selects regions from test images where the LV is fully present, then automatically segments the LV contour. However, the network was limited by the training set, which used only 400 healthy and 12 diseased LV patients. In 2015, U-Net convolutional neural networks (CNN) were first reported for use with medical image segmentation. Large dataset results showed average similarity scores to expert delineations from 89% to 94% across multiple echo systems.

In general, the clinical usefulness of both shape prior and deep learning-based methods is limited by high computational costs and the need for large training datasets. Moreover, both methods impose assumptions on the expected shape of the LV in the image, further hindering the adaptability of such methods.

SUMMARY

Various embodiments of the present application relate to an automated LV segmentation framework which overcomes these gaps by using a modified Dijkstra's algorithm that does not require shape or temporal priors, nor any training. Our approach relies on a feature-based weighting of the shortest-path cost function to yield improved robustness and computation cost.

One aspect of the present application relates to a non-transitory machine readable storage medium having a machine readable program stored therein, wherein the machine readable program, when executed on a processing system, causes the processing system to perform a method of image processing, wherein the method includes reading a plurality of images. The method further includes selecting a set of user defined feature points. Additionally, the method includes transforming a first set of coordinates system of each image of the plurality of images into a second set of coordinates system, thereby producing a second plurality of images, wherein each image of the second plurality of images are represented in the second set of coordinates system. Furthermore, the method includes detecting a plurality of image features from each image of the second plurality of images. The method also includes identifying a connected path of the plurality of image features using the user defined feature points. Next, the method includes iteratively defining the connected path based on a maximum user-defined step size to obtain a plurality of connected paths. Further, the method includes consolidating the plurality of connected paths using a numerical interpolation of radial-basis functions. The method additionally includes outputting coordinates of the consolidated plurality of connected paths.

DETAILED DESCRIPTION

The following disclosure provides many different embodiments, or examples, for implementing different features of the present application. Specific examples of components and arrangements are described below to simplify the present disclosure. These are examples and are not intended to be limiting. The making and using of illustrative embodiments are discussed in detail below. It should be appreciated, however, that the disclosure provides many applicable concepts that can be embodied in a wide variety of specific contexts. In at least some embodiments, one or more embodiment(s) detailed herein and/or variations thereof are combinable with one or more embodiment(s) herein and/or variations thereof.

Automated segmentation methods aim to find a boundary that connects the endpoints of the mitral annulus and optimally represents the LV in a cardiac echo scan. Based on the representation of the LV, the optimal boundary should begin at one mitral annulus (MA) end point, end at the other MA end point, and contain primarily high-intensity pixels. Dijkstra's algorithm is well-suited to identify this path in polar unwrapped scan images. Dijkstra's algorithm (FIG. 1a) is a graph-based procedure that identifies the lowest "cost" path through a node network (i.e image pixels) spanning between a start and end node (i.e., the MA points). However, in its generic form, Dijkstra's algorithm often fails for LV segmentation due to signal dropout, LV clipping, and image noise typically in echo scans as well as the varying contrast-to-noise ratio (CNR) of echo vendors. Further, using all scan image pixels as nodes for Dijkstra's algorithm yields impractically high computational costs. To mitigate these issues, we propose a modified Dijkstra's algorithm which uses a strategic node selection, a novel cost formulation, and an iterative implementation for LV segmentation. A contrast normalization step is also used to yield a method that is both fast and vendor agnostic.

Figure 1A:
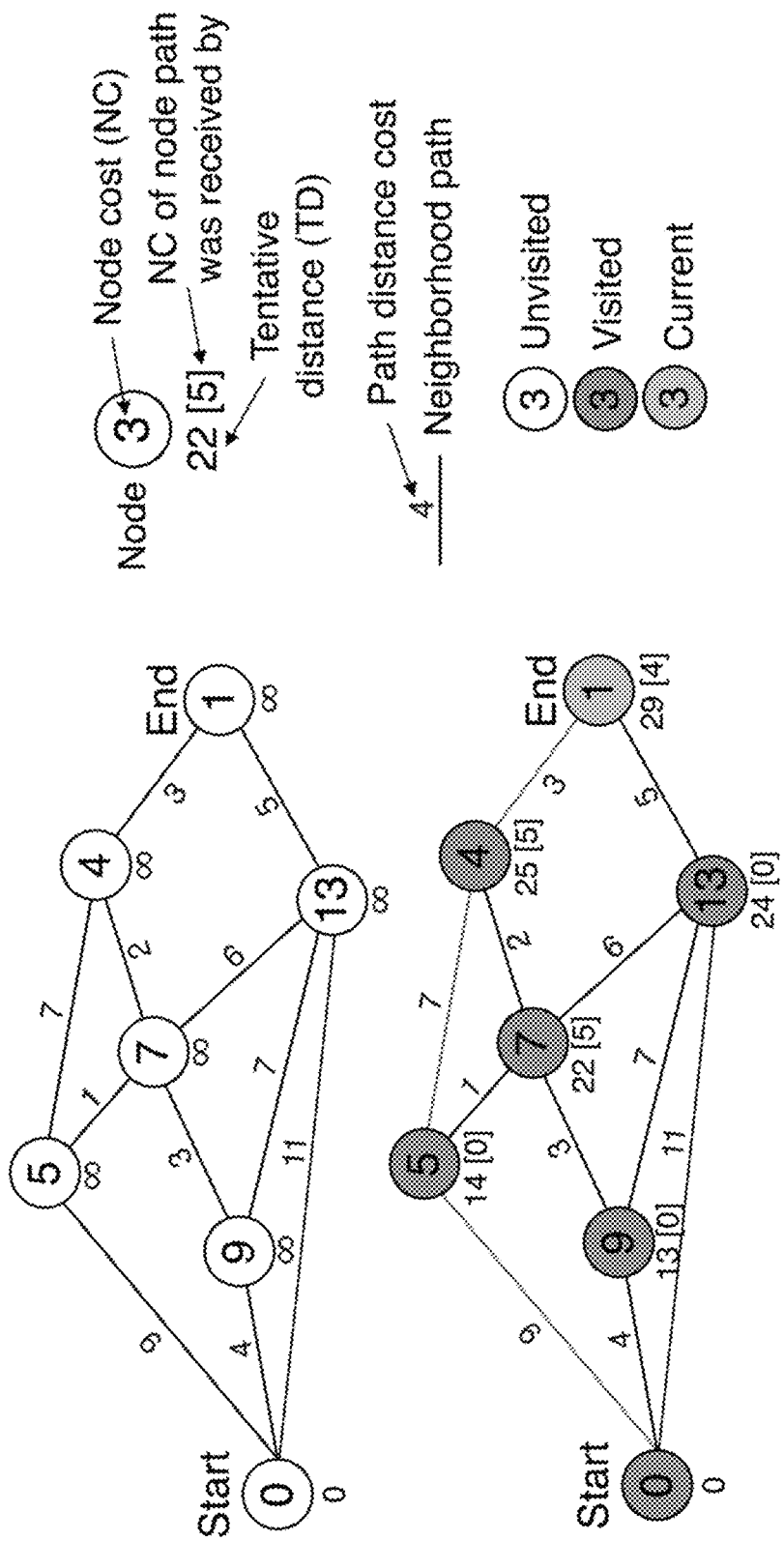
FIG. 1(a) illustrates an example of Dijkstra's algorithm procedure from start (top) to end (bottom).

Basics of Dijkstra's algorithm: For Dijkstra's algorithm, a node network including neighborhood connections and node cost (NC) is first defined. From the start node, the algorithm iteratively marches through the network, "visiting" one node per iteration until the end node is visited. Each node is initially assigned a "tentative distance" (TD) of infinity, except for the starting node, which is assigned a TD of zero, as shown in FIG. 1a. The node TD represents the cost of a path as it passes through that node. From the current node, $n_o$, the cost of the path to travel to each neighboring node, $n_n$, is evaluated as $TD(n_n)_{poss}$. If $TD(n_n)_{poss}$ is less than the neighboring node's current TD, the TD is reassigned as $TD(n_n)_{poss}$. The total path cost typically incorporates the summation of NCs which it passes through and a 'path distance cost' or pathlength. If path smoothness is of interest, a 'path angle cost', based on the angle between nodes, can be included. After each iteration, the next node visited is set as the one with the lowest TD among unvisited nodes.

Figure 1B:
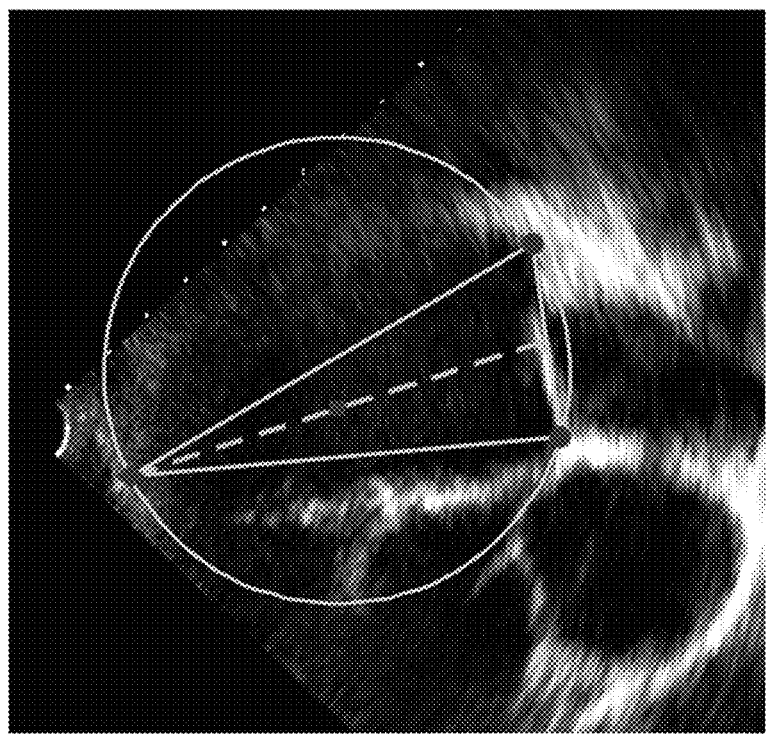
FIG. 1(b) illustrates user input points.
Figure 1C:
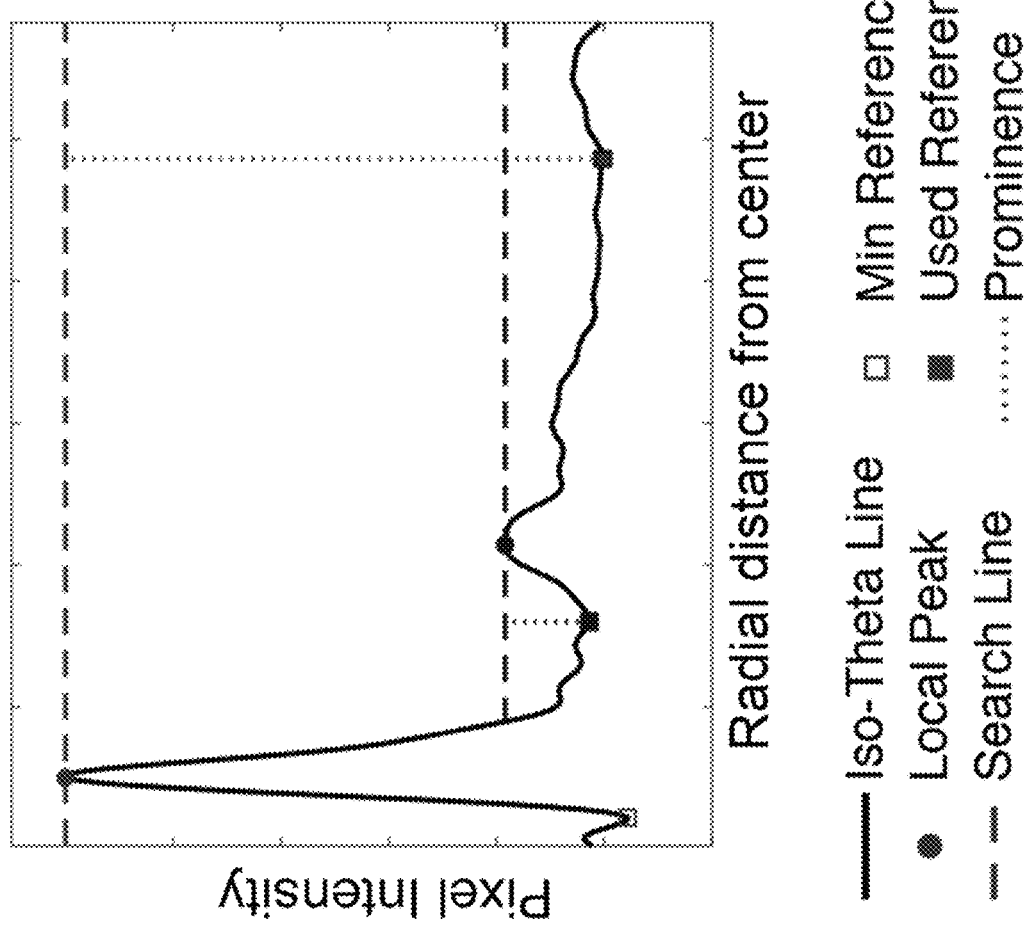
FIG. 1(c) illustrates peak prominence calculation methods for the first (top) and second (bottom) local peaks.

Dijkstra's algorithm requires user-defined start and end nodes. The algorithm is initialized by three user-input point (UIP) selections on an arbitrary scan image (FIG. 1b). The three UIPs are tracked in time using a standard cross-correlation with a 256×256-pixel window. For the LV, these three UIPs correspond to the apex and two ends of the MA. The LV center ($x_c$, $y_c$) is defined as the geometric center of a triangle formed by the three UIPs and is used to transform the images from Cartesian to polar coordinates (r, θ) according to:

$$x_o = x - x_c, \quad (1)$$
$$y_0 = y - y_c,$$
$$r = \sqrt{x_o^2 + y_o^2},$$
$$\theta = \text{atan2}(y_o, x_o)$$

where $x_o$ and $y_o$ are the LV-centered (x, y) and atan 2 is:

$$\text{atan2}(y, x) = \arctan\left(\frac{y}{x}\right) + \frac{\pi}{2}\text{sign}(y) * (1 - \text{sign}(x)). \quad (2)$$

Figure 1D:
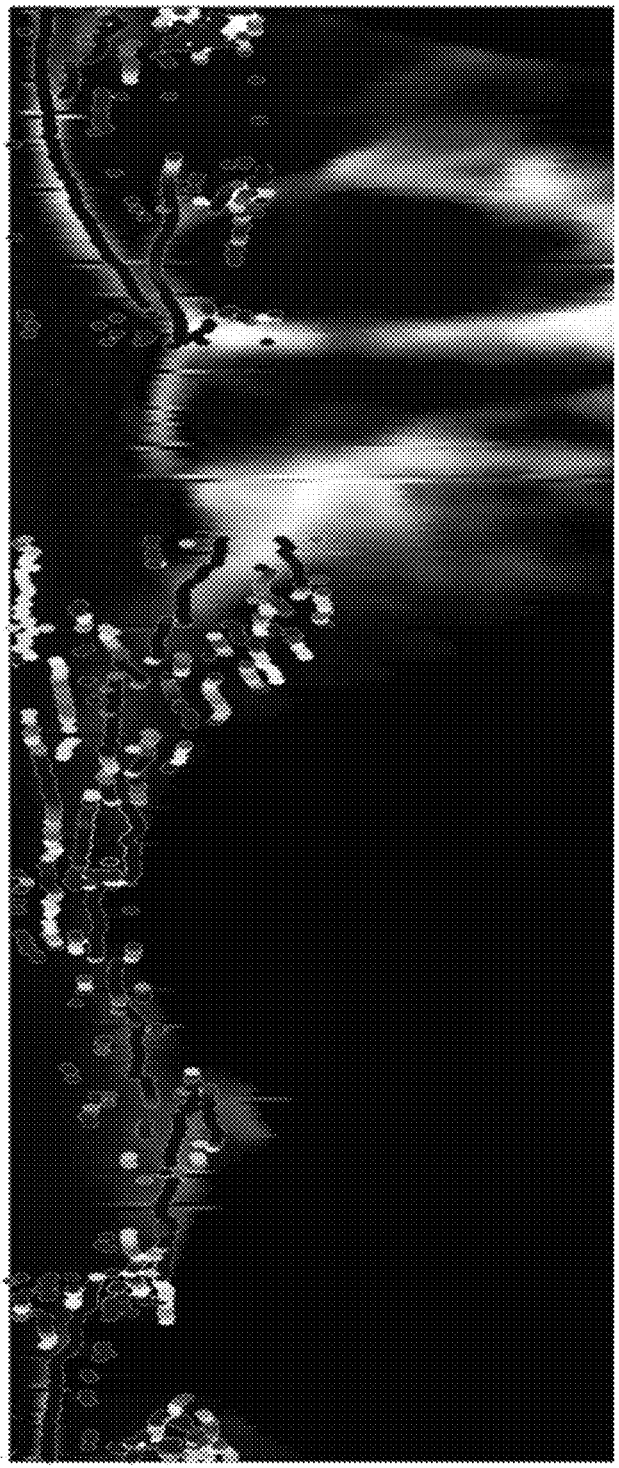
FIG. 1(d) illustrates polar unwrapped image with nodes and node costs.

Using the unwrapped polar images, peaks of image intensity along the iso-theta lines (columns of the image in FIG. 1d) are identified. Only these peak-based nodes that are also within a radial distance (from the LV center) of 1.5× the radius of the circle defined by the UIPs are included. This strategic node selection reduces the node network size by two orders of magnitude, from typically $10^5$ nodes to $10^3$ nodes.

Figure 1E:
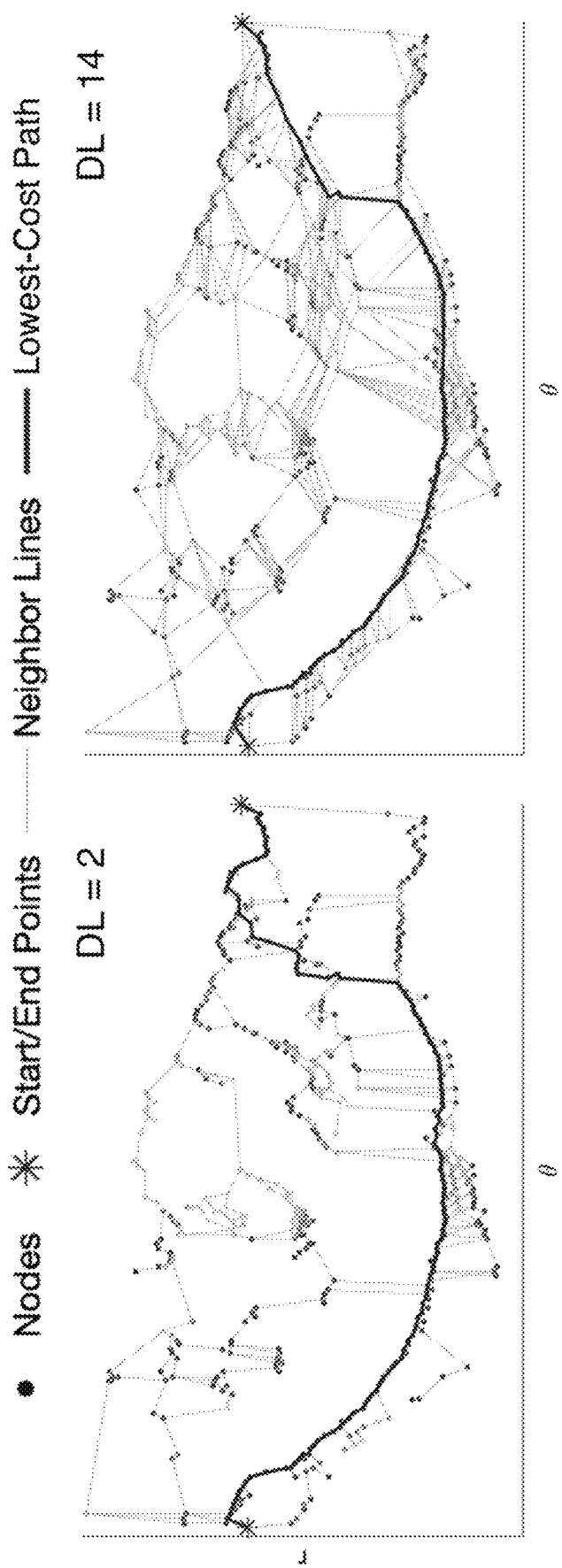
FIG. 1(e) illustrates Dijkstra's algorithm neighborhoods for a DL=2 and DL=14.

For each node, the peak prominence and peak pixel intensity are used for the cost evaluation. Peak prominence quantifies the significance of the node peak intensity relative to other node peaks in the iso-theta line, providing an "uncertainty" for each peak. Peak prominence is computed as the difference between the peak height and a local minimum on the iso-theta line, as depicted in FIG. 1e. The novel NC is then formulated as:

$$NC = (\hat{P} + \hat{I}) \quad (3),$$

where $\hat{P}$ and $\hat{I}$ are the normalized prominence and intensity values, respectively, and are normalized by their respective mean values across all nodes. Nodes with a cost greater than 1.25 times the mean NC of all nodes are discarded as they predominantly add noise and computational cost to the node neighborhood network. A path distance cost, $C_{dist}$, and path angle cost, $C_{angle}$, are defined according to:

$$C_{dist} = \sqrt{r_{n_n}^2 + r_{n_o}^2 - [2 * r_{n_n} * r_{n_o} * (\theta_{n_n} - \theta_{n_o})]}, \quad (4)$$

$$C_{angle} = 0.1 * |90° - \text{atan2}(\theta_{n_n} - \theta_{n_o}, r_{n_n} - r_{n_o})|, \quad (5)$$

where atan 2 is the function defined in Eq. 2, $(r_{n_o}, \theta_{n_o})$ is the location of the currently visited node $n_o$, $(r_{n_n}, \theta_{n_n})$ is the location of the neighboring node $n_n$, and Eq. 4 is evaluated in pixels. Eq. 5 is evaluated in degrees and the '0.1' factor is used to bring NC, $C_{dist}$, and $C_{angle}$ to the same order of magnitude. $TD(n_n)_{pass}$ is evaluated according to:

$$TD(n_n)_{pass} = TD(n_o) + \alpha NC_{n_n} + \gamma C_{angle} + (C_{dist})^\beta \quad (6),$$

where $NC_{n_n}$ is the cost of the neighboring node (Eq. 3), and α, β, and γ are constant regularization coefficients. The constant β enables exponential penalization of large path jumps. A β value of 1.75 is effective for preventing segmentations from cutting through the LV. α and γ are normalizing factors which control the relative weight of the NC vs. path angle cost vs. path distance cost. Because Dijkstra's algorithm is highly sensitive to the range and distribution of the cost matrix, proper setting of these constants is critical. For example, weighting the path angle cost too high biases paths towards a straight line in the polar domain (circle in Cartesian coordinates). A ratio of 10:5:1 of $NC:C_{dist}:C_{angle}$ provided a successful balance for this application. This ratio was achieved using an α=15 and γ=0.2. For other applications the optimal ratio should be explored.

Although strategic node selection reduces the dimension of the problem, it produces a non-structured grid of nodes which complicates the node neighborhood definition. Moreover, with noise and signal dropout, it is at times desirable for paths to "jump" over iso-theta lines with no or noisy nodes. Thus, adjusting the allowable theta-distance limit (DL) between neighboring nodes can yield different paths, as illustrated in FIG. 1e. However, an "optimal" DL for a given image cannot be determined a priori because the presence of noise and image artifacts is challenging to detect. Thus, several iterations of Dijkstra's algorithm are performed, spanning a range of DLs. For the LV, we used a DL ranging from 2° to 14° in increments of 2°, resulting in seven iterations. A DL greater than 14° can yield large boundary jumps that cut off parts of the LV, as a lower number of nodes in the path often yields a lower path cost. Each node is required to have at least one "forward neighbor", at times requiring a DL exception.

Figure 1F:
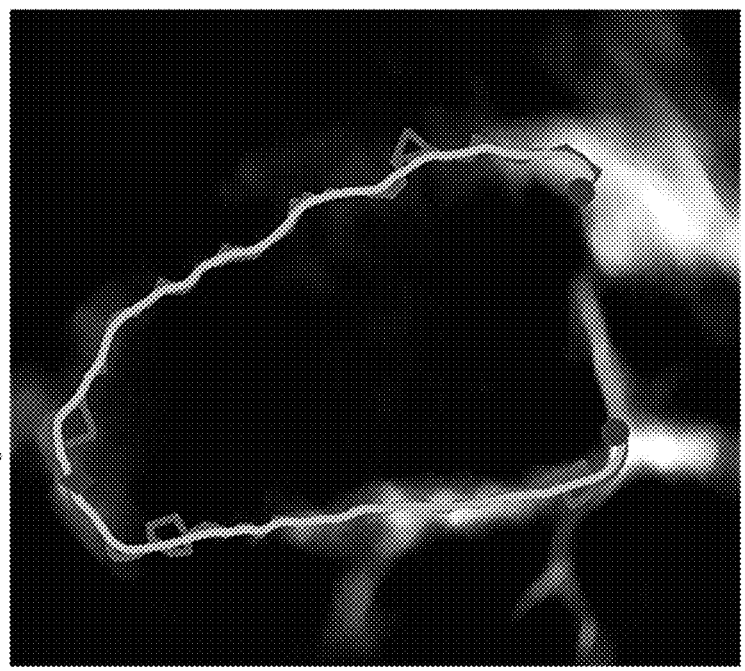
FIG. 1(f) illustrates MQ-RBF boundary fitting of iterative Dijkstra's algorithm boundaries.

To ensure the boundary passes through the LV apex, Dijkstra's algorithm is run from the apex to each MA point separately. A single boundary is fitted from the seven iteration boundaries using a weighted multi-quadratic radial basis function (MQ-RBF), as shown in FIG. 1f. The MQ-RBF weights are set as the mean $\hat{P}$ for each path. Gradient-based smoothing was applied to the MQ-RBF boundaries, followed by median temporal smoothing.

To ensure temporal boundary smoothness, reduce the likelihood of image artifacts corrupting boundaries, and lower computational cost, the nodes used in the modified Dijkstra's algorithm can be initialized by the previous time step's boundary. For initialization, an expected boundary for the current time step is computed by displacing the previous boundary by the average radial displacement of the apex and MV points between the two time steps. Only nodes within a 25% radial distance tolerance of the expected boundary are included in the node network. If the average change between the initialized and previous time step's boundaries is higher than 10%, this often indicates LV regions were clipped, and the current frame is rerun uninitialized.

Using this initialized approach, ProID's selection of the first frame to evaluate, or "start frame", is important since it prescribes the remaining boundaries. If an image with high noise or image artifacts that corrupts the resulting boundary is used as the start frame, the boundary identification for the entire scan time-series will likely fail. To avoid such an issue, five possible starting frames around end diastole of the first recorded beat are evaluated. End diastole was chosen because it typically has the lowest papillary muscle image intensity. Uninitialized boundaries are evaluated using each of the five possible start frames. The time frame whose boundary is closest to the median of these boundaries is selected as the starting frame.

Overall, the proposed algorithm incorporates an enhanced node selection criterion, peak prominence-based node cost assessment, a unique iterative implementation of Dijkstra's algorithm, and a temporally based initialization procedure. For brevity, we term this method the 'prominence-based iterative Dijkstra's' method, or ProID. In its present form ProID does not use any machine learning, nor require training data.

Adaptive contrast enhancement (ACE) was applied to the raw scan images to account for varying contrast-to-noise ratios (CNR) across echo systems and produce evaluation images with similar pixel intensity distributions. ACE scan images, $Im_{ACE}$, are computed according to:

$$Im_{ACE} = \frac{Im_{raw} - I_1}{I_2 - I_2}, \text{ bounded by: } 0 \leq Im_{ACE} \leq 255, \quad (7)$$

where $Im_{raw}$, is the raw scan image, and $I_1$ and $I_2$ are one-half the mean and the maximum pixel values, respectively, along the MV-apex line, which connects the apex and the center of the MV (FIG. 1a). Subsequently, an 11×11-pixel median filter is used to smooth the ACE-enhanced images.

Figure 2A:
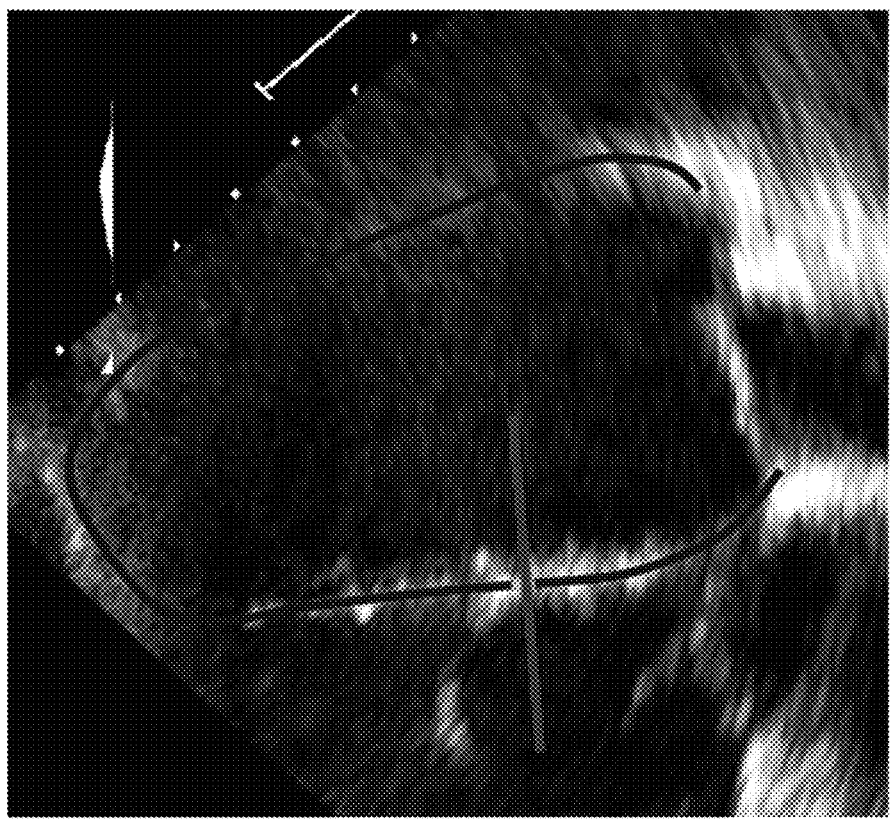
FIG. 2(a) illustrates volume-based boundary correction method where lines are drawn perpendicularly to the boundary.
Figure 2B:
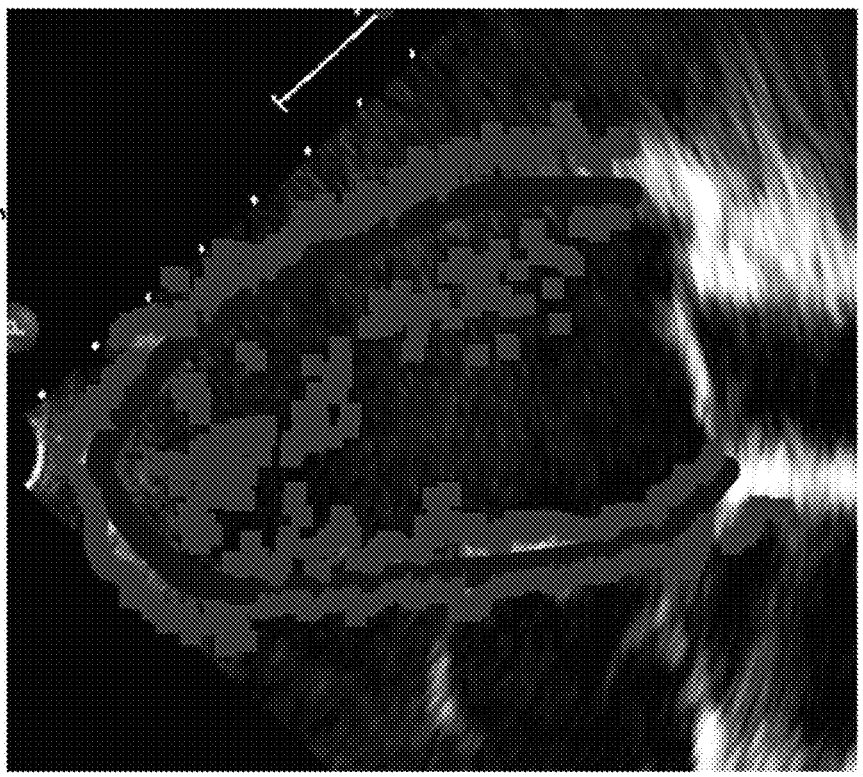
FIG. 2(b) identifies the inner and outer boundary points.
Figure 2C:
FIG. 2(c) illustrates original smoothed boundary, inner and outer boundaries, and corrected boundary for a given scan.

To account for varying clinician segmentation preferences, a volume-based boundary correction step is applied to the ProID boundaries. For each frame, inner and outer boundaries are first identified using a line perpendicular to the smoothed boundary, as shown in FIG. 2a. The outer boundary is defined as the first point radially outwards, where the pixel intensity drops below 67% of that of the boundary point. The inner boundary is defined as the most radially inward point of either the location of a first minimum intensity peak inward of the boundary or the first point whose pixel intensity is less than 25% of the smoothed boundary pixel intensity. A lower threshold was used for the inner boundary to capture the papillary muscles. The inner and outer boundary points are filtered using the discrete wavelet transform applied in polar coordinates and smoothed using the gradient-based and median temporal smoothing. FIGS. 2b and 2c show inner and outer points and boundaries.

The position of each point along the original boundary, $r_b$, relative to the inner (re) and outer ($r_o$) boundaries, or a "relative boundary position (RBP)", is then computed by:

$$RBP = \frac{r_b - r_i}{r_o - r_i}, \quad (8)$$

and can be interpreted as:

$$RBP = \begin{cases} > 1 & r_b \text{ is radially outwards of } r_o \\ 1 & r_b \text{ is located at } r_o \\ 0 & r_b \text{ is located at } r_i \\ < 0 & r_b \text{ is radially inwards of } r_i \\ \text{otherwise} & r_b \text{ is radially betweeen } r_o \text{ and } r_i \end{cases} \quad (9)$$

Figure 2D:
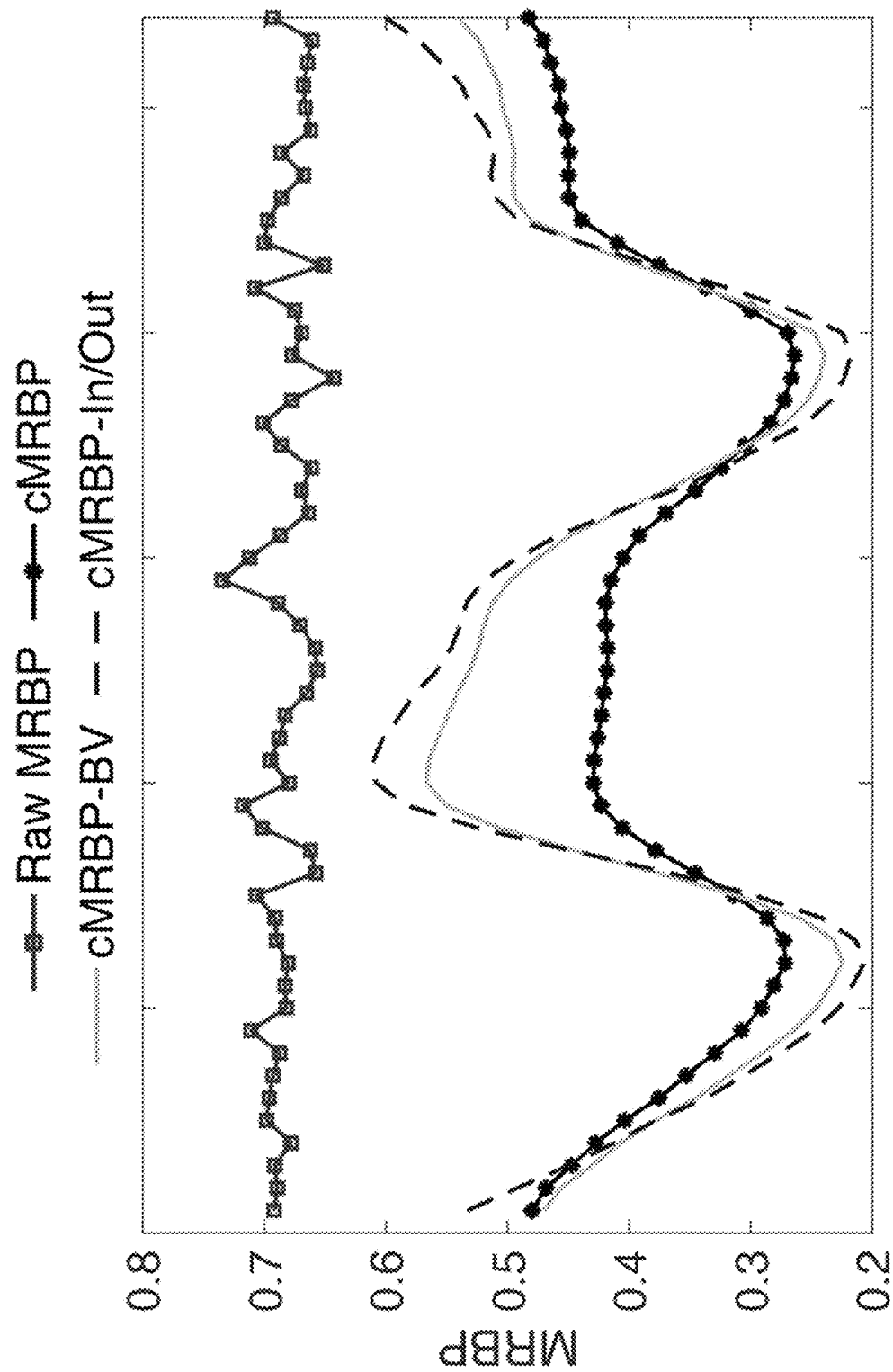
FIG. 2(d) illustrates mean relative boundary position (MRBP).
Figure 2E:
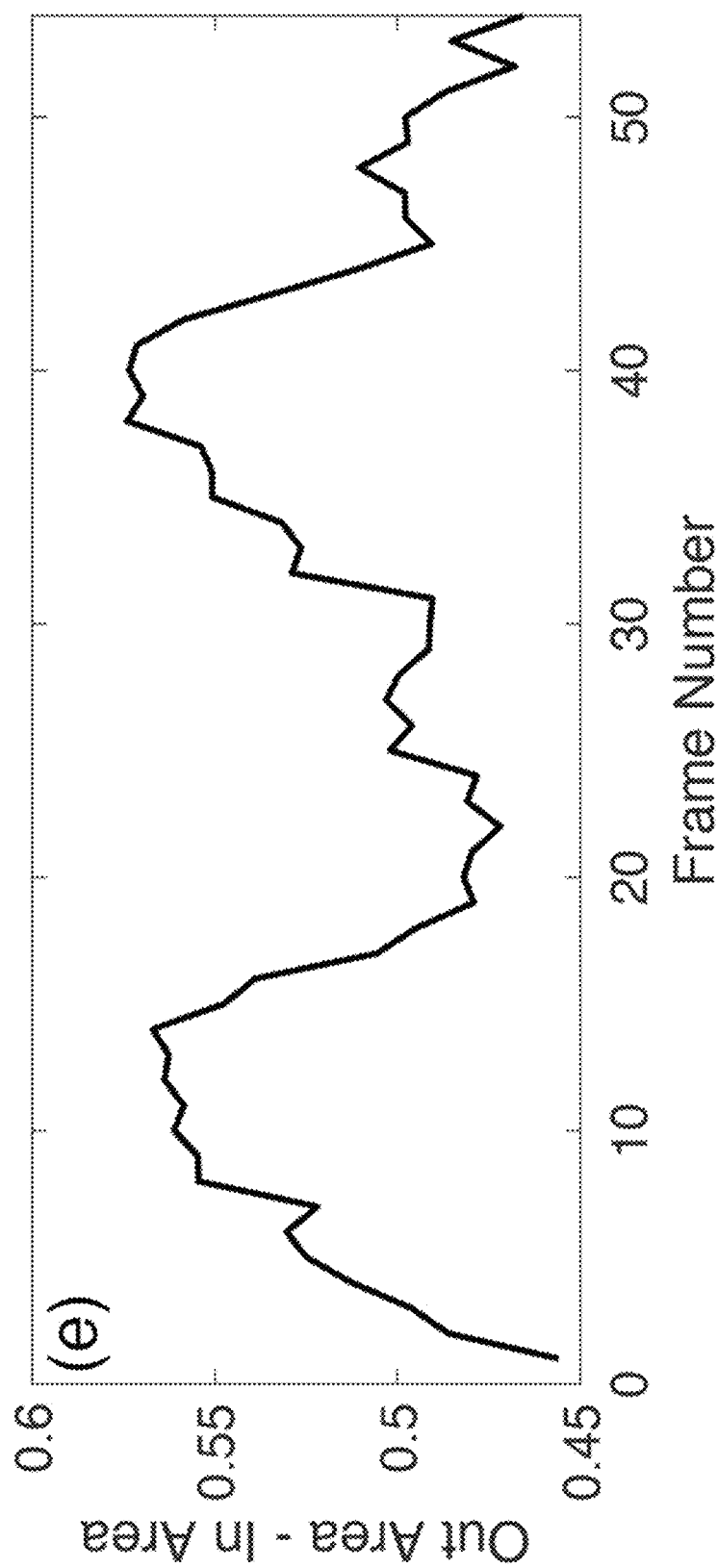
FIG. 2(e) difference in area between inner and outer boundaries across scans.

For each frame, the mean RBP (MRBP) is computed and is considered the "raw MRBP". A desired corrected MRBP (cMRBP) is then assigned to each scan frame. The cMRBP is initially set, as shown in FIG. 2d, by interpolating the raw LV volume array (FIG. 2f) where the average EDV and ESV correspond to cMRBP values of 0.47 and 0.27, respectively. The systolic cMRBP is set lower because papillary muscles maintain higher pixel intensity at systole, which lower the peak prominence computed for the region. This often pushes ProID boundaries radially outward, while clinical boundaries are typically drawn radially inside the papillary muscles. It should be noted that these values were arbitrarily set as well-suited values for the trained readers used herein. Future work should aim to systematically determine optimal values for any reader. The initial cMRBP is adjusted to account for disparities between each beat's diastolic and systolic volumes, as observed in FIG. 2f. The beat variability adjusted cMRBP is denoted as 'cMRBP-BV' in FIG. 2d. The cMRBP (denoted as 'cMRBP-In/Out' in FIG. 2d) is then adjusted to account for differences in the area between the inner and outer boundaries across frames (FIG. 2e) which can produce a bias in the scaling. 'cMRBP-In/Out' is used for boundary scaling.

Figure 2F:
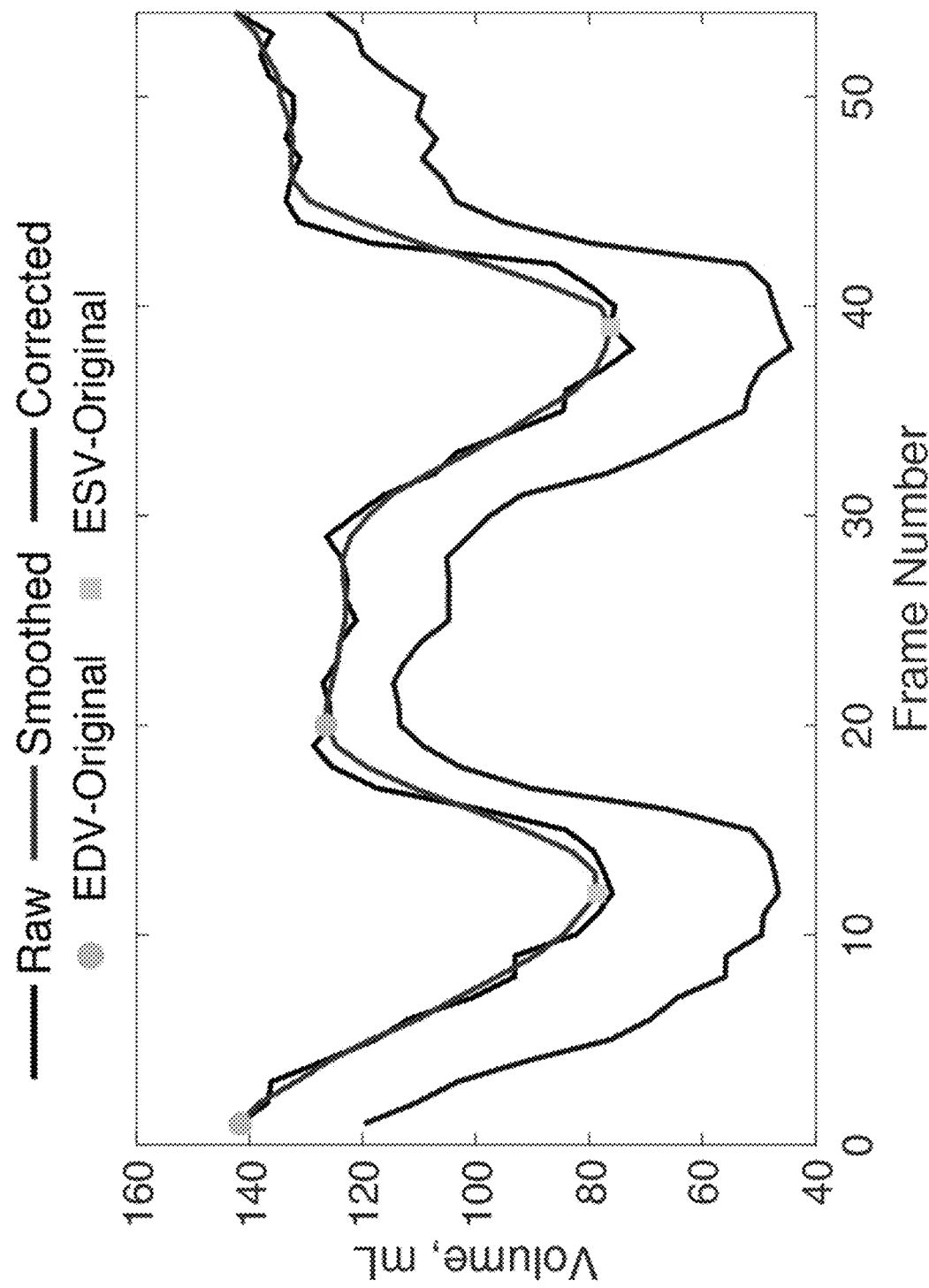
FIG. 2(f) raw, smoothed, and corrected LV volumes.

The volume-based correction is done by scaling the original boundary such that the MRBP of the corrected boundary matches its assigned cMRBP. For example, Frame 1 of the scan shown in FIG. 2d the MRBP should be adjusted from 0.69 to 0.53 by moving the boundary radially inward. A power-six scaling is used to adjust the RBP of each boundary point, so points furthest from the cMRBP are corrected most. FIGS. 2c and 2f show the volume-corrected boundary.

Example 1

A non-transitory machine readable storage medium having a machine readable program stored therein, wherein the machine readable program, when executed on a processing system, causes the processing system to perform a method of image processing, wherein the method includes reading a plurality of images. The method further includes selecting a set of user defined feature points. Additionally, the method includes transforming a first set of coordinates system of each image of the plurality of images into a second set of coordinates system, thereby producing a second plurality of images, wherein each image of the second plurality of images are represented in the second set of coordinates system. Furthermore, the method includes detecting a plurality of image features from each image of the second plurality of images. The method also includes identifying a connected path of the plurality of image features using the user defined feature points. Next, the method includes iteratively defining the connected path based on a maximum user-defined step size to obtain a plurality of connected paths. Further, the method includes consolidating the plurality of connected paths using a numerical interpolation of radial-basis functions. The method additionally includes outputting coordinates of the consolidated plurality of connected paths.

In at least one embodiment, the first set of coordinates system includes Cartesian coordinates. In one or more embodiments, the second set of coordinates system includes at least one of a log-polar coordinate system, polar coordinate system, or log-log coordinate system. In some embodiments, the plurality of image features includes at least one of local peaks of image intensity, local peaks of gradient intensity, local peaks of color intensity, or local peaks of color-gradient intensity.

In one or more embodiments, the detecting the plurality of image features from each image of the second plurality of images includes evaluating a prominence of the plurality of image features. The prominence includes at least one of a ratio of a first amplitude of a local peak of image intensity of the local peaks of image intensity and a second amplitude of the local peaks of image intensity; a ratio of a first amplitude of a local peak of gradient intensity of the local peaks of gradient intensity and a second amplitude of the local peaks of gradient intensity; a ratio of a first amplitude of a local peak of color intensity of the local peaks of color intensity and a second amplitude of the local peaks of color intensity; or a ratio of a first amplitude of a local peak of color-gradient intensity of the local peaks of color-gradient intensity and a second amplitude of the local peaks of color-gradient intensity.

In one or more embodiments, the detecting the plurality of image features from each image of the second plurality of images includes evaluating a significance of the plurality of image features. The significance includes at least one of a ratio of a first amplitude of a local peak of image intensity of the local peaks of image intensity and a second user-defined value of image intensity of the second plurality of images; a ratio of a first amplitude of a local peak of gradient intensity of the local peaks of gradient intensity and a second user-defined value of gradient intensity of the second plurality of images; a ratio of a first amplitude of a local peak of color intensity of the local peaks of color intensity and a second user-defined value of color intensity of the second plurality of images; or a ratio of a first amplitude of a local peak of color-gradient intensity of the local peaks of color-gradient intensity and a second user-defined value of color-gradient intensity of the second plurality of images.

In at least one embodiment, the identifying the connected path of the plurality of image features includes defining a cost function of each image of the second plurality of image features based on the prominence. Additionally, the method includes establishing a connectivity map of each of the image features from the plurality of image features, thereby producing a plurality of connectivity maps. Furthermore, the method includes identifying a lowest cost path from the plurality of connectivity maps based on the cost function, wherein a start and an end of the connected path is the set of user defined feature points.

In one or more embodiments, the identifying the connected path of the plurality of image features includes defining a cost function of each image of the second plurality of image features based on the significance. The method further includes establishing a connectivity map of each of the image features from the plurality of image features, thereby producing a plurality of connectivity maps. Additionally, the method includes identifying a lowest cost path from the plurality of connectivity maps based on the cost function, wherein a start and an end of the connected path is the set of user defined feature points.

In some embodiments, the plurality of image features includes at least one of local peaks of image texture, local peaks of gradient texture, local peaks of color texture, or local peaks of color-gradient texture. In some embodiments, the plurality of image features includes at least one of local peaks of image shape descriptors, local peaks of gradient shape descriptors, local peaks of color shape descriptors, or local peaks of color-gradient shape descriptors.

In one or more embodiments, the detecting the plurality of image features from each image of the second plurality of images includes evaluating a prominence of the plurality of image features. The prominence includes at least one of: a ratio of a first amplitude of a local peak of image texture of the local peaks of image texture and a second amplitude of the local peaks of image texture; a ratio of a first amplitude of a local peak of gradient texture of the local peaks of gradient texture and a second amplitude of the local peaks of gradient texture; a ratio of a first amplitude of a local peak of color texture of the local peaks of color texture and a second amplitude of the local peaks of color texture; or a ratio of a first amplitude of a local peak of color-gradient texture of the local peaks of color-gradient texture and a second amplitude of the local peaks of color-gradient texture.

In one or more embodiments, the detecting the plurality of image features from each image of the second plurality of images includes evaluating a significance of the plurality of image features. The significance includes at least one of: a ratio of a first amplitude of a local peak of image texture of the local peaks of image texture and a second amplitude of the local peaks of image texture; a ratio of a first amplitude of a local peak of gradient texture of the local peaks of gradient texture and a second amplitude of the local peaks of gradient texture; a ratio of a first amplitude of a local peak of color texture of the local peaks of color texture and a second amplitude of the local peaks of color texture; or a ratio of a first amplitude of a local peak of color-gradient texture of the local peaks of color-gradient texture and a second amplitude of the local peaks of color-gradient texture.

In at least one embodiment, the identifying the connected path of the plurality of image features includes defining a cost function of each image of the second plurality of image features based on the prominence. The method further includes establishing a connectivity map of each of the image features from the plurality of image features, thereby producing a plurality of connectivity maps. Additionally, the method includes identifying a lowest cost path from the plurality of connectivity maps based on the cost function, wherein a start and an end of the connected path is the set of user defined feature points.

In at least one embodiment, the identifying the connected path of the plurality of image features includes defining a cost function of each image of the second plurality of image features based on the significance. The method further includes establishing a connectivity map of each of the image features from the plurality of image features, thereby producing a plurality of connectivity maps. Additionally, the method includes identifying a lowest cost path from the plurality of connectivity maps based on the cost function, wherein a start and an end of the connected path is the set of user defined feature points.

In one or more embodiments, the detecting the plurality of image features from each image of the second plurality of images includes evaluating a prominence of the plurality of image features. The prominence includes at least one of: a ratio of a first amplitude of a local peak of image shape descriptor of the local peaks of image shape descriptor and a second amplitude of the local peaks of image shape descriptor; a ratio of a first amplitude of a local peak of gradient shape descriptor of the local peaks of gradient shape descriptor and a second amplitude of the local peaks of gradient shape descriptor; a ratio of a first amplitude of a local peak of color shape descriptor of the local peaks of color shape descriptor and a second amplitude of the local peaks of color shape descriptor; or a ratio of a first amplitude of a local peak of color-gradient shape descriptor of the local peaks of color-gradient shape descriptor and a second amplitude of the local peaks of color-gradient shape descriptor.

In one or more embodiments, the detecting the plurality of image features from each image of the second plurality of images includes evaluating a significance of the plurality of image features. The significance includes at least one of: a ratio of a first amplitude of a local peak of image shape descriptor of the local peaks of image shape descriptor and a second amplitude of the local peaks of image shape descriptor; a ratio of a first amplitude of a local peak of gradient shape descriptor of the local peaks of gradient shape descriptor and a second amplitude of the local peaks of gradient shape descriptor; a ratio of a first amplitude of a local peak of color shape descriptor of the local peaks of color shape descriptor and a second amplitude of the local peaks of color shape descriptor; or a ratio of a first amplitude of a local peak of color-gradient shape descriptor of the local peaks of color-gradient shape descriptor and a second amplitude of the local peaks of color-gradient shape descriptor.

In at least one embodiment, the identifying the connected path of the plurality of image features includes defining a cost function of each image of the second plurality of image features based on the prominence. The method further includes establishing a connectivity map of each of the image features from the plurality of image features, thereby producing a plurality of connectivity maps. Additionally, the method includes identifying a lowest cost path from the plurality of connectivity maps based on the cost function, wherein a start and an end of the connected path is the set of user defined feature points.

In at least one embodiment, the identifying the connected path of the plurality of image features includes defining a cost function of each image of the second plurality of image features based on the significance. Additionally, the method includes establishing a connectivity map of each of the image features from the plurality of image features, thereby producing a plurality of connectivity maps. Furthermore, the method includes identifying a lowest cost path from the plurality of connectivity maps based on the cost function, wherein a start and an end of the connected path is the set of user defined feature points.

Various embodiments of the present application also relate to a system architecture operating the above methods, discretized by different protocols.

Figure 3:
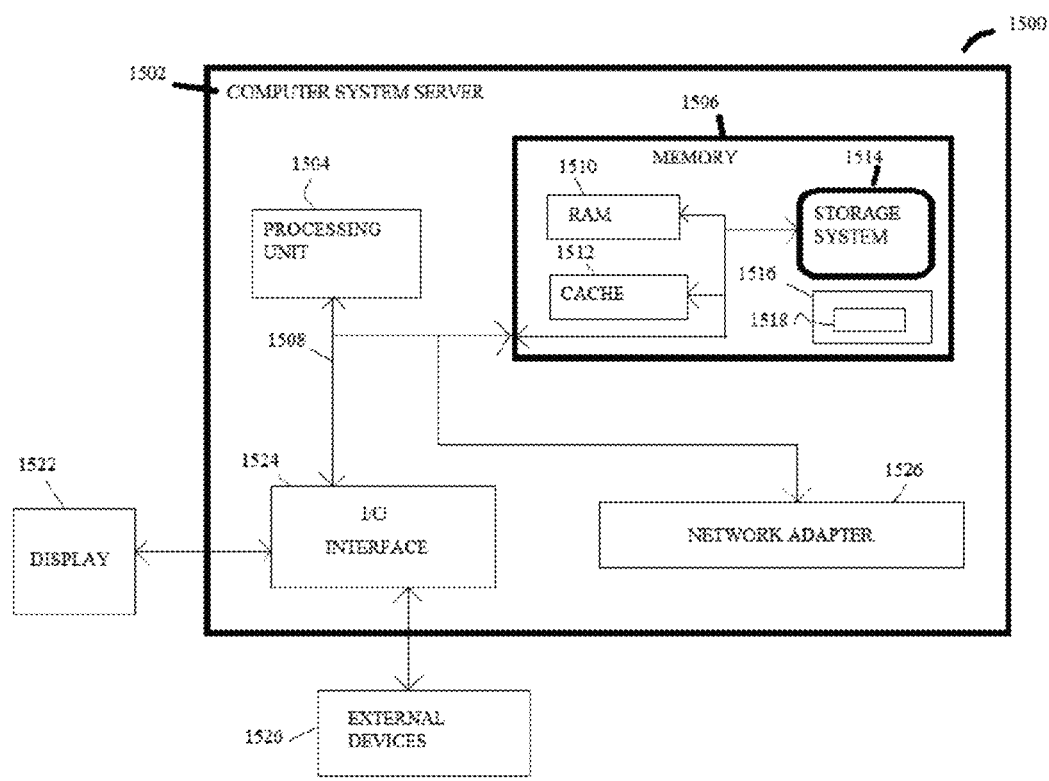
FIG. 3 illustrates one example of a computing or processing node 1500 for executing the method or the software architecture of the present application.

FIG. 3 illustrates one example of a computing or processing node 1500 for executing the above method or the software architecture. This is not intended to suggest any limitation as to the scope of use or functionality of embodiments of the invention described herein. Regardless, the computing node 1500 is capable of being implemented and/or performing any of the functionality set forth hereinabove.

In computing node 1500 there is a computer system/server 1502, which is operational with numerous other general purpose or special purpose computing system environments or configurations. Examples of well-known computing systems, environments, and/or configurations that may be suitable for use with computer system/server 1502 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 1502 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 502 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 3, computer system/server 1502 in cloud computing node 1500 is shown in the form of a general-purpose computing device. The components of computer system/server 1502 may include, but are not limited to, one or more processors or processing units 1504, a system memory 1506, and a bus 1508 that couples various system components including system memory 1506 to processor 1504.

Bus 1508 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system/server 1502 typically includes a variety of computer system readable media. Such media may be any available media that is accessible by computer system/server 1502, and it includes both volatile and non-volatile media, removable and non-removable media.

System memory 1506, in one embodiment, implements the above methods and the software architectures. The system memory 506 can include computer system readable media in the form of volatile memory, such as random access memory (RAM) 1510 and/or cache memory 1512. Computer system/server 1502 may further include other removable/non-removable, volatile/non-volatile computer system storage media. By way of example only, storage system 1514 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 1508 by one or more data media interfaces. As will be further depicted and described below, memory 1506 may include at least one program product having a set (e.g., at least one) of program modules that are configured to carry out the functions of various embodiments of the invention.

Program/utility 1516, having a set (at least one) of program modules 1518, may be stored in memory 1506 by way of example, and not limitation, as well as an operating system, one or more application programs, other program modules, and program data. Each of the operating system, one or more application programs, other program modules, and program data or some combination thereof, may include an implementation of a networking environment. Program modules 1518 generally carry out the functions and/or methodologies of various embodiments of the invention as described herein.

As will be appreciated by one skilled in the art, aspects of the present invention may be embodied as a system, method, or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Computer system/server 1502 may also communicate with one or more external devices 1520 such as a keyboard, a pointing device, a display 1522, etc.; one or more devices that enable a user to interact with computer system/server 1502; and/or any devices (e.g., network card, modem, etc.) that enable computer system/server 1502 to communicate with one or more other computing devices. Such communication can occur via I/O interfaces 1524. Still yet, computer system/server 1502 can communicate with one or more networks such as a local area network (LAN), a general wide area network (WAN), and/or a public network (e.g., the Internet) via network adapter 1526. As depicted, network adapter 1526 communicates with the other components of computer system/server 1502 via bus 1508. It should be understood that although not shown, other hardware and/or software components could be used in conjunction with computer system/server 1502. Examples, include, but are not limited to: microcode, device drivers, redundant processing units, external disk drive arrays, RAID systems, tape drives, and data archival storage systems, etc.

Although the present disclosure and its advantages have been described in detail, it should be understood that various changes, substitutions and alterations can be made herein without departing from the spirit and scope of the disclosure as defined by the appended claims. Moreover, the scope of the present application is not intended to be limited to the particular embodiments of the process, design, machine, manufacture, and composition of matter, means, methods and steps described in the specification. As one of ordinary skill in the art will readily appreciate from the disclosure, processes, machines, manufacture, compositions of matter, means, methods, or steps, presently existing or later to be developed, that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

While several embodiments have been provided in the present disclosure, it should be understood that the disclosed systems and methods might be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted, or not implemented.

The invention claimed is:

1. A non-transitory machine readable storage medium having a machine readable program stored therein, wherein the machine readable program, when executed on a processing system, causes the processing system to perform a method of image processing, wherein the method comprises:
   reading a plurality of images;
   selecting a set of user defined feature points;
   transforming a first set of coordinates system of each image of the plurality of images into a second set of coordinates system, thereby producing a second plurality of images, wherein each image of the second plurality of images are represented in the second set of coordinates system;
   detecting a plurality of image features from each image of the second plurality of images;
   identifying a connected path of the plurality of image features using the user defined feature points;
   iteratively defining the connected path based on a maximum user-defined step size to obtain a plurality of connected paths;
   consolidating the plurality of connected paths using a numerical interpolation of radial-basis functions; and
   outputting coordinates of the consolidated plurality of connected paths.

2. The method of claim 1, wherein the first set of coordinates system comprises Cartesian coordinates.

3. The method of claim 1, wherein the second set of coordinates system comprises at least one of a log-polar coordinate system, polar coordinate system, or log-log coordinate system.

4. The method of claim 1, wherein the plurality of image features comprises at least one of local peaks of image intensity, local peaks of gradient intensity, local peaks of color intensity, or local peaks of color-gradient intensity.

5. The method of claim 4, wherein the detecting the plurality of image features from each image of the second plurality of images comprises:
   evaluating a prominence of the plurality of image features, wherein the prominence comprises at least one of:

a ratio of a first amplitude of a local peak of image intensity of the local peaks of image intensity and a second amplitude of the local peaks of image intensity;

a ratio of a first amplitude of a local peak of gradient intensity of the local peaks of gradient intensity and a second amplitude of the local peaks of gradient intensity;

a ratio of a first amplitude of a local peak of color intensity of the local peaks of color intensity and a second amplitude of the local peaks of color intensity; or a ratio of a first amplitude of a local peak of color-gradient intensity of the local peaks of color-gradient intensity and a second amplitude of the local peaks of color-gradient intensity.

6. The method of claim 4, wherein the detecting the plurality of image features from each image of the second plurality of images comprises:

evaluating a significance of the plurality of image features, wherein the significance comprises at least one of:

a ratio of a first amplitude of a local peak of image intensity of the local peaks of image intensity and a second user-defined value of image intensity of the second plurality of images;

a ratio of a first amplitude of a local peak of gradient intensity of the local peaks of gradient intensity and a second user-defined value of gradient intensity of the second plurality of images;

a ratio of a first amplitude of a local peak of color intensity of the local peaks of color intensity and a second user-defined value of color intensity of the second plurality of images; or a ratio of a first amplitude of a local peak of color-gradient intensity of the local peaks of color-gradient intensity and a second user-defined value of color-gradient intensity of the second plurality of images.

7. The method of claim 5, wherein the identifying the connected path of the plurality of image features comprises:

defining a cost function of each image of the second plurality of image features based on the prominence;

establishing a connectivity map of each of the image features from the plurality of image features, thereby producing a plurality of connectivity maps; and identifying a lowest cost path from the plurality of connectivity maps based on the cost function, wherein a start and an end of the connected path is the set of user defined feature points.

8. The method of claim 6, wherein the identifying the connected path of the plurality of image features comprises:

defining a cost function of each image of the second plurality of image features based on the significance;

establishing a connectivity map of each of the image features from the plurality of image features, thereby producing a plurality of connectivity maps; and identifying a lowest cost path from the plurality of connectivity maps based on the cost function, wherein a start and an end of the connected path is the set of user defined feature points.

9. The method of claim 1, wherein the plurality of image features comprises at least one of local peaks of image texture, local peaks of gradient texture, local peaks of color texture, or local peaks of color-gradient texture.

10. The method of claim 1, wherein the plurality of image features comprises at least one of local peaks of image shape descriptors, local peaks of gradient shape descriptors, local peaks of color shape descriptors, or local peaks of color-gradient shape descriptors.

11. The method of claim 9, wherein the detecting the plurality of image features from each image of the second plurality of images comprises:

evaluating a prominence of the plurality of image features, wherein the prominence comprises at least one of:

a ratio of a first amplitude of a local peak of image texture of the local peaks of image texture and a second amplitude of the local peaks of image texture;

a ratio of a first amplitude of a local peak of gradient texture of the local peaks of gradient texture and a second amplitude of the local peaks of gradient texture;

a ratio of a first amplitude of a local peak of color texture of the local peaks of color texture and a second amplitude of the local peaks of color texture; or a ratio of a first amplitude of a local peak of color-gradient texture of the local peaks of color-gradient texture and a second amplitude of the local peaks of color-gradient texture.

12. The method of claim 9, wherein the detecting the plurality of image features from each image of the second plurality of images comprises:

evaluating a significance of the plurality of image features, wherein the significance comprises at least one of:

a ratio of a first amplitude of a local peak of image texture of the local peaks of image texture and a second amplitude of the local peaks of image texture;

a ratio of a first amplitude of a local peak of gradient texture of the local peaks of gradient texture and a second amplitude of the local peaks of gradient texture;

a ratio of a first amplitude of a local peak of color texture of the local peaks of color texture and a second amplitude of the local peaks of color texture; or a ratio of a first amplitude of a local peak of color-gradient texture of the local peaks of color-gradient texture and a second amplitude of the local peaks of color-gradient texture.

13. The method of claim 11, wherein the identifying the connected path of the plurality of image features comprises:

defining a cost function of each image of the second plurality of image features based on the prominence;

establishing a connectivity map of each of the image features from the plurality of image features, thereby producing a plurality of connectivity maps; and identifying a lowest cost path from the plurality of connectivity maps based on the cost function, wherein a start and an end of the connected path is the set of user defined feature points.

14. The method of claim 12, wherein the identifying the connected path of the plurality of image features comprises:

defining a cost function of each image of the second plurality of image features based on the significance;

establishing a connectivity map of each of the image features from the plurality of image features, thereby producing a plurality of connectivity maps; and identifying a lowest cost path from the plurality of connectivity maps based on the cost function, wherein a start and an end of the connected path is the set of user defined feature points.

15. The method of claim 10, wherein the detecting the plurality of image features from each image of the second plurality of images comprises:
evaluating a prominence of the plurality of image features, wherein the prominence comprises at least one of:
- a ratio of a first amplitude of a local peak of image shape descriptor of the local peaks of image shape descriptor and a second amplitude of the local peaks of image shape descriptor;
- a ratio of a first amplitude of a local peak of gradient shape descriptor of the local peaks of gradient shape descriptor and a second amplitude of the local peaks of gradient shape descriptor;
- a ratio of a first amplitude of a local peak of color shape descriptor of the local peaks of color shape descriptor and a second amplitude of the local peaks of color shape descriptor; or
- a ratio of a first amplitude of a local peak of color-gradient shape descriptor of the local peaks of color-gradient shape descriptor and a second amplitude of the local peaks of color-gradient shape descriptor.

16. The method of claim 10, wherein the detecting the plurality of image features from each image of the second plurality of images comprises:
evaluating a significance of the plurality of image features, wherein the significance comprises at least one of:
- a ratio of a first amplitude of a local peak of image shape descriptor of the local peaks of image shape descriptor and a second amplitude of the local peaks of image shape descriptor;
- a ratio of a first amplitude of a local peak of gradient shape descriptor of the local peaks of gradient shape descriptor and a second amplitude of the local peaks of gradient shape descriptor;
- a ratio of a first amplitude of a local peak of color shape descriptor of the local peaks of color shape descriptor and a second amplitude of the local peaks of color shape descriptor; or
- a ratio of a first amplitude of a local peak of color-gradient shape descriptor of the local peaks of color-gradient shape descriptor and a second amplitude of the local peaks of color-gradient shape descriptor.

17. The method of claim 15, wherein the identifying the connected path of the plurality of image features comprises:
defining a cost function of each image of the second plurality of image features based on the prominence;
establishing a connectivity map of each of the image features from the plurality of image features, thereby producing a plurality of connectivity maps; and
identifying a lowest cost path from the plurality of connectivity maps based on the cost function, wherein a start and an end of the connected path is the set of user defined feature points.

18. The method of claim 16, wherein the identifying the connected path of the plurality of image features comprises:
defining a cost function of each image of the second plurality of image features based on the significance;
establishing a connectivity map of each of the image features from the plurality of image features, thereby producing a plurality of connectivity maps; and
identifying a lowest cost path from the plurality of connectivity maps based on the cost function, wherein a start and an end of the connected path is the set of user defined feature points.

* * * * *